United States Patent
Karinka et al.

(10) Patent No.: US 8,236,166 B2
(45) Date of Patent: Aug. 7, 2012

(54) NO CALIBRATION ANALYTE SENSORS AND METHODS

(75) Inventors: Shridhara Alva Karinka, Pleasanton, CA (US); Yi Wang, San Ramon, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 1053 days.

(21) Appl. No.: 12/110,026

(22) Filed: Apr. 25, 2008

(65) Prior Publication Data

US 2009/0011449 A1    Jan. 8, 2009

Related U.S. Application Data

(60) Provisional application No. 60/914,590, filed on Apr. 27, 2007.

(51) Int. Cl.
*G01N 27/26* (2006.01)

(52) U.S. Cl. .................. 205/792; 205/777.5; 205/775

(58) Field of Classification Search ............. 204/403.01–403.15; 205/777.5, 205/778, 792

See application file for complete search history.

(56) References Cited

U.S. PATENT DOCUMENTS

| | | | |
|---|---|---|---|
| 6,544,475 B1* | 4/2003 | Douglas et al. | 422/402 |
| 6,592,745 B1* | 7/2003 | Feldman et al. | 205/777.5 |
| 7,819,161 B2* | 10/2010 | Neel et al. | 156/510 |
| 7,918,012 B2* | 4/2011 | Wang et al. | 29/593 |
| 2006/0091006 A1* | 5/2006 | Wang et al. | 204/403.02 |

* cited by examiner

*Primary Examiner* — Alex Noguerola
(74) *Attorney, Agent, or Firm* — Edward J. Baba; Marcus T. Hunt; Bozicevic, Field & Francis LLP

(57) ABSTRACT

A meter and sensors, for use in combination, where no calibration code has to be entered by the user or is read by the meter. The meter is configured with a predetermined slope and y-intercept built into the meter. If the slope and y-intercept of the sensor are within a predetermined area or grid, or otherwise close to the slope and y-intercept of the meter, the batch of sensors is acceptable for use with that meter for providing accurate analyte concentration results.

14 Claims, 6 Drawing Sheets

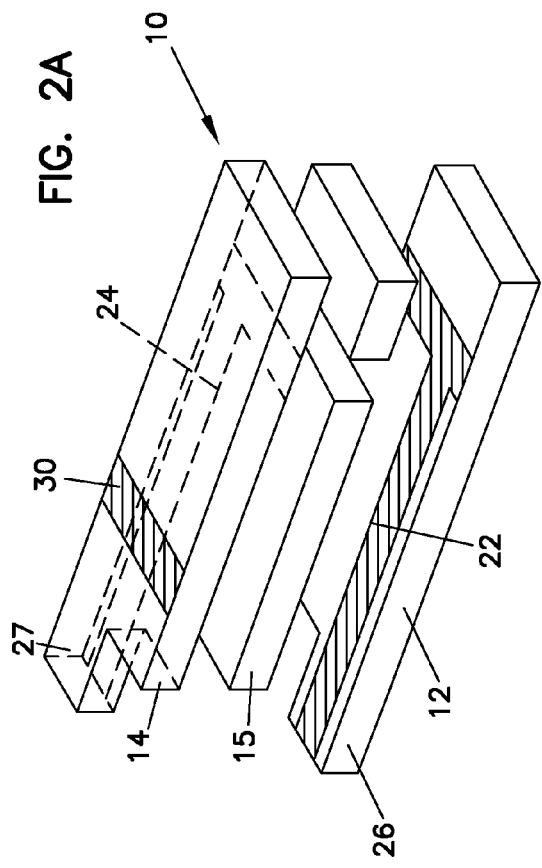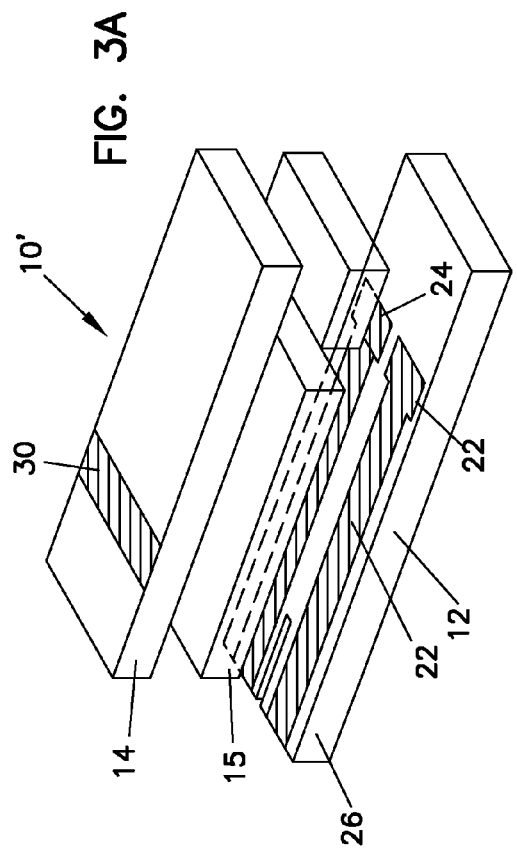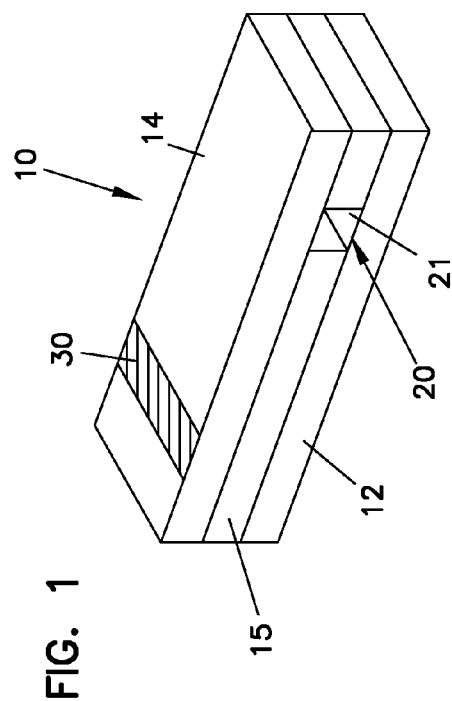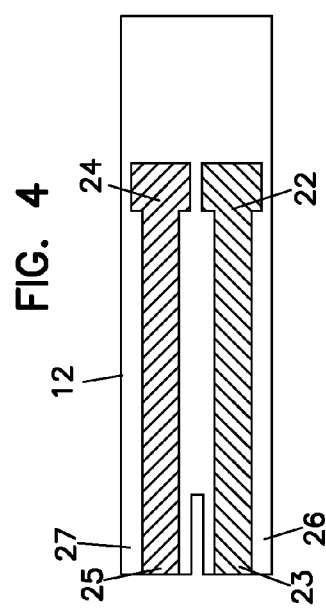

NO CALIBRATION ANALYTE SENSORS AND METHODS

CROSS REFERENCE TO RELATED APPLICATIONS

This Application claims priority to U.S. Provisional Application No. 60/914,590 filed on Apr. 27, 2007, titled "NO CALIBRATION ANALYTE SENSORS AND METHODS," the disclosure of which is hereby incorporated by reference in its entirety.

BACKGROUND

Biosensors, also referred to as analytical sensors or merely sensors, are commonly used to determine the presence and concentration of a biological analyte in a sample. Such biosensors are used, for example, to monitor blood glucose levels in diabetic patients.

As sensors continue to be used, there continues to be an interest in sensors that are easy to manufacture and easy for a patient to use.

SUMMARY

The present disclosure provides sensors and methods for the detection and quantification of an analyte in a sample. The sensors are configured to provide a clinically accurate analyte level reading, without the user having to enter a calibration code or the like that corresponds to the sensor. The sensors are configured to be used with a meter that has a predetermined calibration code present therein. Embodiments of the sensor are provided, by the manufacturer of the sensors, with a configuration that provides a standardized calibration.

In general, certain embodiments of the present disclosure include sensors for analysis of an analyte in a sample, e.g., a small volume sample, by, for example, coulometry, amperometry and/or potentiometry. The sensors include at least a working electrode and a counter electrode, which may be on the same substrate (e.g., co-planar) or may be on different substrates (e.g., facing). The sensors also include a sample chamber to hold the sample in electrolytic contact with the working electrode. A sensor according to the present disclosure may utilize an electron transfer agent and/or a redox mediator. The sensors may be made with at least one substrate and configured for side-filling, tip-filling, or top-filling. In addition, in some embodiments, the sensor may be part of an integrated sample acquisition and analyte measurement device. An integrated sample acquisition and analyte measurement device may include a sensor and a skin piercing member, so that the device can be used to pierce the skin of a user to cause flow of a fluid sample, such as blood, that may then be collected by the sensor. In at least some embodiments, the fluid sample may be collected without moving the integrated sample acquisition and analyte measurement device.

Various embodiments of methods of making sensors, according to this disclosure, include providing a sample chamber and/or measurement zone having an electrode surface area that, when filled with a sample to be tested, provides a clinically accurate analyte level reading, without the user having to enter a calibration code or the like that corresponds to the sensor, into a meter that is used to read the sensor. The meter is configured with a predetermined slope and y-intercept built into the meter. If the slope and y-intercept (which relate to the calibration code) of the sensor are within a predetermined area or grid, or otherwise close to the slope and y-intercept of the meter, the batch of sensors is acceptable for use with that meter.

In certain embodiments, one particular method of forming a sensor, as described further below, includes forming at least one working electrode on a first substrate and forming at least one counter or counter/reference electrode on a second substrate. A spacer layer is disposed on either the first or second substrates. The spacer layer defines a chamber into which a sample may be drawn and held when the sensor is completed. Chemistry for detecting one or more analytes may be present on the first or second substrate in a region that will be exposed within the sample chamber when the sensor is completed. The first and second substrates may then be brought together and spaced apart by the spacer layer with the sample chamber providing access to the at least one working electrode and the at least one counter or counter/reference electrode. Any or all of the volume of the sample chamber, the volume of the measurement zone, the surface area of the electrode(s) within the sample chamber and/or measurement zone, may be adjusted during the manufacturing process so that the resulting sensor meets certain criteria.

Certain other embodiments include forming at least one working electrode on a first substrate and forming at least one counter or counter/reference electrode on the same, first substrate. One or two additional layers may be added to define a chamber into which a sample may be drawn and held when the sensor is completed. Chemistry may be present in a region that will be exposed within the sample chamber when the sensor is completed. The substrates may then be brought together, forming a sample chamber providing access to the at least one working electrode and the at least one counter or counter/reference electrode. In some embodiments, the volume of the sample chamber, and optionally the volume of the measurement zone, may be adjusted so that the resulting sensor meets certain criteria. Adjusting the volume of the sample chamber may or may not modify the electrode area. Additionally or alternately, in some embodiments, the surface area of the at least one working electrode and/or the at least one counter or counter/reference electrode are adjusted so that the resulting sensor meets certain criteria. Adjusting the electrode area may or may not modify the volume of the sample chamber.

These and various other features which characterize some embodiments according to the present disclosure are pointed out with particularity in the attached claims. For a better understanding of the embodiments, their advantages, and objectives obtained by their use, reference should be made to the drawings and to the accompanying description, in which there is illustrated and described particular embodiments according to the present disclosure.

BRIEF DESCRIPTION OF THE DRAWINGS

Referring now to the drawings, wherein like reference numerals and letters indicate corresponding structure throughout the several views:

FIG. 1 is a schematic perspective view of a first embodiment of a sensor strip in accordance with the present disclosure;

FIG. 2A is an exploded view of the sensor strip shown in FIG. 1, the layers illustrated individually with the electrodes in a first configuration;

FIG. 3A is a schematic view of a second embodiment of a sensor strip in accordance with the present disclosure, the layer illustrated individually with the electrodes in a second configuration;

FIG. 4 is a top view of the first substrate of the sensor strip of FIGS. 3A and 3B;

DETAILED DESCRIPTION

Figure 2B:
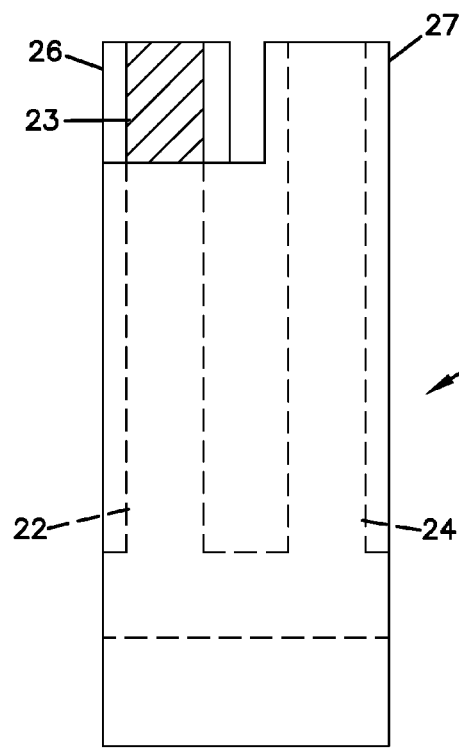
FIG. 2B is a top view of the sensor strip shown in FIGS. 1 and 2A.

In some currently available analyte testing systems, a value indicative of the calibration code of a sensor is manually entered into the meter or other equipment, for example, by the user. Based on the calibration code, the meter uses one of several programs or parameters stored within the meter. In other currently available systems, the sensor calibration code is directly read by the meter or other equipment, thus not requiring input or other interaction by the user. These sensors, however, still have a calibration code associated with them, which includes slope and y-intercept values. The slope and y-intercept values are used to determine the analyte concentration based on the measured signal. The calibration code, whether inputted manually or automatically, is needed to standardize the analysis results received from non-standardized sensors. In other words, different sensors vary, e.g., from lot to lot, a sufficient amount that, if no compensation were made, the results would differ from sensor to sensor and the results could be clinically inaccurate.

The sensors of this disclosure are calibration-adjusted to a pre-determined calibration (slope and y-intercept), during the manufacturing process, to avoid the need for the user to input or otherwise set a calibration code for the sensor or perform other calibration procedure(s) before using the sensor. The sensors of this disclosure are also calibration-adjusted to avoid the need for the meter to read a calibration code.

This disclosure also provides methods for making sensors that avoid the need for the user to input or otherwise set a calibration code for the sensor, or perform other calibration procedure(s) before using the sensor. The approach described here does not require any additional steps from the user to perform a test. The manufacturing is simple and does not require special packaging or encoding the strips with calibration information.

In general, the calibration code is a combination of slope and intercept or any other mathematical relationship between a measured signal and the concentration of the analyte in the sample.

In some manufacturing process for sensors, the calibration parameters vary from sensor batch (e.g., batch of 1,000, 5,000, etc. sensors) to sensor batch, due to variations in the composition of the active chemistry and/or variations in any inactive components. The present disclosure provides sensors and methods of making sensors in a manner so that the calibration information does not change from one batch to the other.

Referring to the Drawings in general and FIGS. 1 and 2A in particular, a first embodiment of a sensor strip 10 is schematically illustrated. Sensor strip 10 has a first substrate 12, a second substrate 14, and a spacer 15 positioned therebetween. Sensor strip 10 includes at least one working electrode 22 and at least one counter electrode 24. Sensor strip 10 also includes an optional insertion monitor 30.

Sensor Strips

Referring to FIGS. 1, 2A and 2B in particular, sensor strip 10 has first substrate 12, second substrate 14, and spacer 15 positioned therebetween. Sensor strip 10 includes working electrode 22, counter electrode 24 and insertion monitor 30. Sensor strip 10 is a layered construction, in certain embodiments having a generally rectangular shape, i.e., its length is longer than its width, although other shapes are possible as well. Sensor strip 10' of FIGS. 3A and 3B also has first substrate 12, second substrate 14, spacer 15, working electrode 22, counter electrode 24 and insertion monitor 30.

The dimensions of a sensor may vary. In certain embodiments, the overall length of sensor strip 10, 10' may be no less than about 20 mm and no greater than about 50 mm. For example, the length may be between about 30 and 45 mm; e.g., about 30 to 40 mm. It is understood, however that shorter and longer sensor strips 10, 10' could be made. In certain embodiments, the overall width of sensor strip 10, 10' may be no less than about 3 mm and no greater than about 15 mm. For example, the width may be between about 4 and 10 mm, about 5 to 8 mm, or about 5 to 6 mm. In one particular example, sensor strip 10, 10' has a length of about 32 mm and a width of about 6 mm. In another particular example, sensor strip 10, 10' has a length of about 40 mm and a width of about 5 mm. In yet another particular example, sensor strip 10, 10' has a length of about 34 mm and a width of about 5 mm.

Substrates

As provided above, sensor strip 10, 10' has first and second substrates 12, 14, non-conducting, inert substrates which form the overall shape and size of sensor strip 10, 10'. Substrates 12, 14 may be substantially rigid or substantially flexible; in some embodiments, one substrate may be rigid and the other substrate may be flexible. In certain embodiments, substrates 12, 14 are flexible or deformable. Examples of suitable materials for substrates 12, 14 include, but are not limited to, polyester, polyethylene, polycarbonate, polypropylene, nylon, and other "plastics" or polymers. In certain embodiments the substrate material is "Melinex" polyester. Other non-conducting materials may also be used.

Spacer Layer

As indicated above, positioned between substrate 12 and substrate 14 can be spacer 15 to separate first substrate 12 from second substrate 14. Spacer 15 is an inert non-conducting substrate, typically at least as flexible and deformable (or as rigid) as substrates 12, 14. In certain embodiments, spacer 15 is an adhesive layer or double-sided adhesive tape or film. Any adhesive selected for spacer 15 should be selected to not diffuse or release material which may interfere with accurate analyte measurement. Spacer 15 may be generally the same size as substrates 12, 14 or may occupy less than the width and/or length of substrates 12, 14.

In certain embodiments, the thickness of spacer 15 may be at least about 0.01 mm (10 μm) and no greater than about 1 mm or about 0.5 mm. For example, the thickness may be between about 0.02 mm (20 μm) and about 0.2 mm (200 μm).

In one certain embodiment, the thickness is about 0.05 mm (50 μm), and about 0.1 mm (100 μm) in another embodiment.

Sample Chamber

Figure 5:
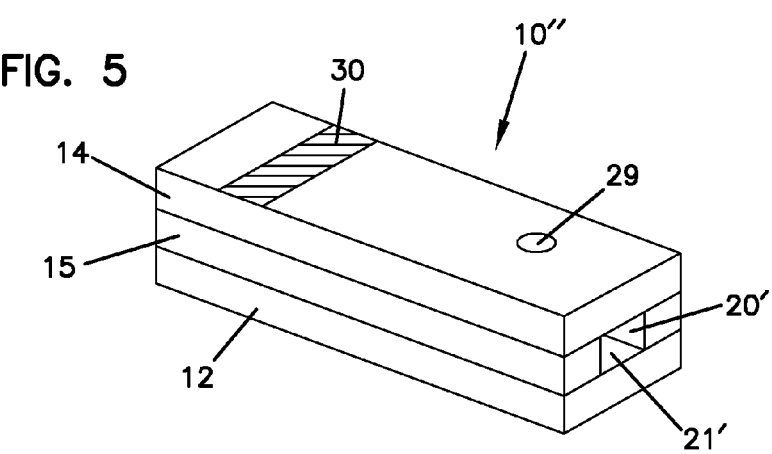
FIG. 5 is a schematic perspective view of another embodiment of a sensor strip in accordance with the present disclosure.

The sensor includes a sample chamber for receiving a volume of sample to be analyzed; in the embodiment illustrated, particularly in FIG. 1, sensor strip 10, 10' includes sample chamber 20 having an inlet 21 for access to sample chamber 20. In the embodiments illustrated, sensor strips 10, 10' are side-fill sensor strips, having inlet 21 present on a side edge of strips 10, 10'. Tip-fill sensors can also be configured in accordance with the present disclosure. Referring to FIG. 5, a tip-filled sensor strip 10" is illustrated. Similar to sensor strips 10, 10', sensor strip 10" has substrates 12, 14 with spacer 15 therebetween and an insertion indicator 30. Sensor strip 10", however, has a sample chamber 20' that extends from an inlet 21' positioned at a tip of sensor strip". Sensor strip 10" includes a vent hole 29 in substrate 14 to facilitate drawing of sample into sample chamber 20' via inlet 21'. It is noted that hole 29, in some embodiments, could be used as a sample inlet.

Sample chamber 20, 20' is configured so that when a sample is provided in chamber 20, 20', the sample is in electrolytic contact with both the working electrode and the counter electrode, which allows electrical current to flow between the electrodes to effect the electrolysis (electrooxidation or electroreduction) of the analyte.

Sample chamber 20, 20' is defined by substrate 12, substrate 14 and spacer 15; in many embodiments, sample chamber 20, 20' exists between substrate 12 and substrate 14 where spacer 15 is not present. Typically, a portion of spacer 15 is removed to provide an area between substrates 12, 14 without spacer 15; this volume of removed spacer is sample chamber 20, 20'. For embodiments that include spacer 15 between substrates 12, 14, the thickness of sample chamber 20, 20' is generally the thickness of spacer 15. Other methods for forming sample chamber 20, 20' could additionally or alternately be used.

Sample chamber 20, 20' has a volume sufficient to receive a sample of biological fluid therein. In some embodiments, such as when sensor strip 10, 10', 10" is a small volume sensor, sample chamber 20, 20' has a volume that is preferably no more than about 1 μL, for example no more than about 0.5 μL, and also for example, no more than about 0.25 μL. A volume of no more than about 0.1 μL is also suitable for sample chamber 20, as are volumes of no more than about 0.05 μL and about 0.03 μL.

A measurement zone is contained within sample chamber 20, 20' and is the region of the sample chamber that contains only that portion of the sample that is interrogated during the analyte assay. In some designs, the measurement zone has a volume that is approximately equal to the volume of sample chamber 20, 20'. In some embodiments the measurement zone includes 80% of the sample chamber, 90% in other embodiments, and about 100% in yet other embodiments.

As provided above, the thickness of sample chamber 20, 20' corresponds typically to the thickness of spacer 15. Particularly for facing electrode configurations, this thickness is small to promote rapid electrolysis of the analyte, as more of the sample will be in contact with the electrode surface for a given sample volume. In addition, a thin sample chamber 20, 20' helps to reduce errors from diffusion of analyte into the measurement zone from other portions of the sample chamber during the analyte assay, because diffusion time is long relative to the measurement time, which may be about 5 seconds or less.

Electrodes

As provided above, the sensor includes a working electrode and at least one counter electrode. The counter electrode may be a counter/reference electrode. If multiple counter electrodes are present, one of the counter electrodes will be a counter electrode and one or more may be reference electrodes. Referring to FIGS. 2A and 2B and FIGS. 3A, 3B and 4, two examples of suitable electrode configurations are illustrated.

Working Electrode

At least one working electrode is positioned on one of first substrate 12 and second substrate 14. In all of FIGS. 2A though 4, working electrode 22 is illustrated on substrate 12. Working electrode 22 extends from the sample chamber 20 to the other end of the sensor 10 as an electrode extension called a "trace". The trace provides a contact pad 23 for providing electrical connection to a meter or other device to allow for data and measurement collection, as will be described later. Contact pad 23 can be positioned on a tab 26 that extends from the substrate on which working electrode 22 is positioned, such as substrate 12. In one embodiment, a tab has more than one contact pad positioned thereon. In a second embodiment, a single contact pad is used to provide a connection to one or more electrodes; that is, multiple electrodes are coupled together and are connected via one contact pad.

Working electrode 22 can be a layer of conductive material such as gold, carbon, platinum, ruthenium dioxide, palladium, or other non-corroding, conducting material. Working electrode 22 can be a combination of two or more conductive materials. An example of a suitable conductive epoxy is ECCOCOAT CT5079-3 Carbon-Filled Conductive Epoxy Coating (available from W.R. Grace Company, Woburn, Mass.). The material of working electrode 22 typically has relatively low electrical resistance and is typically electrochemically inert over the potential range of the sensor during operation.

Working electrode 22 may be applied on substrate 12 by any of various methods, including by being deposited, such as by vapor deposition or vacuum deposition or otherwise sputtered, printed on a flat surface or in an embossed or otherwise recessed surface, transferred from a separate carrier or liner, etched, or molded. Suitable methods of printing include screen-printing, piezoelectric printing, ink jet printing, laser printing, photolithography, and painting.

As provided above, at least a portion of working electrode 22 is provided in sample chamber 20 for the analysis of analyte, in conjunction with the counter electrode.

Counter Electrode

Figure 3B:
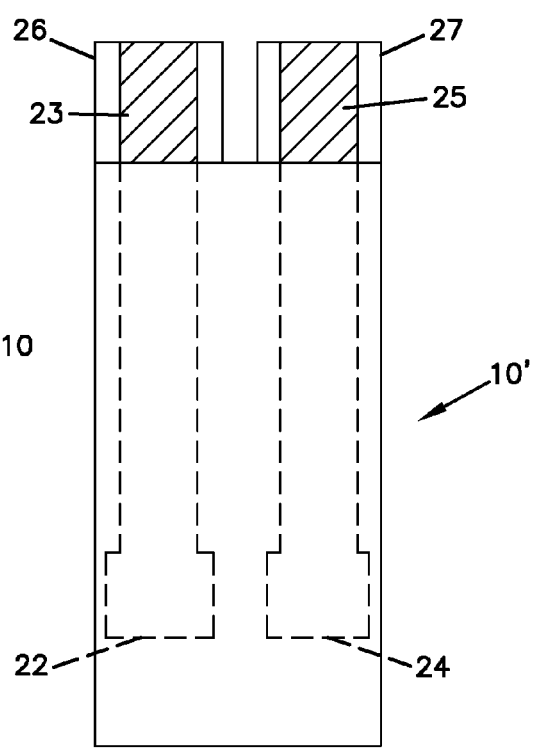
FIG. 3B is a top view of the sensor strip shown in FIG. 3A.

The sensor includes at least one counter electrode positioned within the sample chamber. In FIGS. 2A and 2B, counter electrode 24 is illustrated on substrate 14. In FIGS. 3A, 3B and 4, a counter electrode 24 is present on substrate 12. Counter electrode 24 extends from the sample chamber 20 to the other end of the sensor 10 as an electrode extension called a "trace". The trace provides a contact pad 25 for providing electrical connection to a meter or other device to allow for data and measurement collection, as will be described later. Contact pad 25 can be positioned on a tab 27 that extends from the substrate on which counter electrode 24 is positioned, such as substrate 12 or 14. In one embodiment, a tab has more than one contact pad positioned thereon. In a second embodiment, a single contact pad is used to provide a connection to one or more electrodes; that is, multiple electrodes are coupled together and are connected via one contact pad.

Counter electrode 24 may be constructed in a manner similar to working electrode 22. Suitable materials for the counter/reference or reference electrode include Ag/AgCl or Ag/AgBr on a non-conducting base material or silver chloride on a silver metal base. The same materials and methods may be used for counter electrode 24 as are available for working electrode 22, although different materials and methods may also be used. Counter electrode 24 can include a mix of multiple conducting materials, such as Ag/AgCl and carbon.

Electrode Configurations

Working electrode 22 and counter electrode 24 may be disposed opposite to and facing each other to form facing electrodes. See for example, FIG. 2A, which has working electrode 22 on substrate 12 and counter electrode 24 on substrate 14, forming facing electrodes. In this configuration, the sample chamber is typically present between the two electrodes 22, 24. For this facing electrode configuration, electrodes 22, 24 may be separated by a distance of no more than about 0.2 mm (e.g., at least one portion of the working electrode is separated from one portion of the counter electrode by no more than about 200 μm), e.g., no more than about 100 μm, e.g., no more than about 50 μm.

Working electrode 22 and counter electrode 24 can alternately be positioned generally planar to one another, such as on the same substrate, to form co-planar or planar electrodes. Referring to FIGS. 3A and 4, both working electrode 22 and counter electrode 24 occupy a portion of the surface of substrate 12, thus forming co-planar electrodes.

Sensing Chemistry

In addition to working electrode 22, sensing chemistry material(s) are preferably provided in sample chamber 20, 20' for the analysis of the analyte. Sensing chemistry material facilitates the transfer of electrons between working electrode 22 and the analyte in the sample. Any sensing chemistry may be used in sensor strip 10, 10', 10"; the sensing chemistry may include one or more materials.

The sensing chemistry can be diffusible or leachable, or non-diffusible or non-leachable. For purposes of discussion herein, the term "diffusible" will be used to represent "diffusible or leachable" and the term "non-diffusible" will be used to represent "non-diffusible or non-leachable" and variations thereof. Placement of sensing chemistry components may depend on whether they are diffusible or not. For example, both non-diffusible and/or diffusible component(s) may form a sensing layer on working electrode 22. Alternatively, one or more diffusible components may be present on any surface in sample chamber 20 prior to the introduction of the sample to be analyzed. As another example, one or more diffusible component(s) may be placed in the sample prior to introduction of the sample into sample chamber 20.

Electron Transfer Agent

The sensing chemistry generally includes an electron transfer agent that facilitates the transfer of electrons to or from the analyte. The electron transfer agent may be diffusible or non-diffusible, and may be present on working electrode 22 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes can be used for other analytes.

The electron transfer agent facilitates a current between working electrode 22 and the analyte and enables the electrochemical analysis of molecules. The agent facilitates the transfer electrons between the electrode and the analyte.

Redox Compound

This sensing chemistry may, additionally to or alternatively to the electron transfer agent, include a redox compound such as a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator can be a polymeric redox mediator, or, a redox polymer (i.e., a polymer having one or more redox species). Examples of suitable redox mediators and redox polymer are disclosed in U.S. Pat. No. 6,338,790, for example, and in U.S. Pat. Nos. 6,605,200 and 6,605,201.

If the redox mediator is non-diffusible, then the redox mediator may be disposed on working electrode 22 as a layer. In an embodiment having a redox mediator and an electron transfer agent, if the redox mediator and electron transfer agent are both non-leachable, then both components are disposed on working electrode 22 as individual layers, or combined and applied as a single layer.

The redox mediator, whether it is diffusible or not, mediates a current between working electrode 22 and the analyte and enables the electrochemical analysis of molecules which may not be suited for direct electrochemical reaction on an electrode. The mediator functions as an agent to transfer electrons between the electrode and the analyte.

Sorbent Material

Sample chamber 20 can be empty before the sample is placed in the chamber, or, in some embodiments, the sample chamber can include a sorbent material to sorb and hold a fluid sample during the measurement process. The sorbent material facilitates the uptake of small volume samples by a wicking action which can complement or, e.g., replace any capillary action of the sample chamber. Suitable sorbent materials include polyester, nylon, cellulose, and cellulose derivatives such as nitrocellulose. In addition to or alternatively, a portion or the entirety of the wall of the sample chamber may be coated by a surfactant, which is intended to lower the surface tension of the fluid sample and improve fluid flow within the sample chamber.

Methods other than the wicking action of a sorbent can be used to transport the sample into the sample chamber or measurement zone. Examples of such methods for transport include the application of pressure on a sample to push it into the sample chamber, the creation of a vacuum by a pump or other vacuum-producing method in the sample chamber to pull the sample into the chamber, capillary action due to interfacial tension of the sample with the walls of a thin sample chamber, as well as the wicking action of a sorbent material.

Fill Indicator Electrode

In some instances, it is desirable to be able to determine when the sample chamber is filled. Sensor strip 10, 10', 10" can be indicated as filled, or substantially filled, by observing a signal between an indicator electrode and one or both of working electrode 22 or counter electrode 24 as sample chamber 20 fills with fluid. When fluid reaches the indicator electrode, the signal from that electrode will change. Suitable signals for observing include, for example, voltage, current, resistance, impedance, or capacitance between the indicator electrode and, for example, working electrode 22. Alternatively, the sensor can be observed after filling to determine if a value of the signal (e.g., voltage, current, resistance, impedance, or capacitance) has been reached indicating that the sample chamber is filled. Typically, the indicator electrode is further downstream from a sample inlet, such as inlet 21, than working electrode 22 and counter electrode 24.

The sensor or equipment that the sensor connected is with (e.g., a meter) can include a sign (e.g., a visual sign or auditory signal) that is activated in response to the indicator electrode to alert the user that the measurement zone has been sufficiently filled. The sensor or equipment can be configured to initiate a reading when the indicator electrode indicates that the measurement zone has been filled with or without alerting the user. The reading can be initiated, for example, by applying a potential between the working electrode and the counter electrode and beginning to monitor the signals generated at the working electrode.

Insertion Monitor

The sensor can include an indicator to notify when proper insertion of sensor strip 10, 10, 10''' into receiving equipment, such as a meter, has occurred. As seen in FIGS. 1, 2A, 2B, 3A, 3B and 5, sensor strips 10, 10', 10" include insertion monitor 30 on an exterior surface of one of substrates 12, 14. Conductive insertion monitor 30 is positioned on the non-conductive base substrate and has a contact pad for electrical contact with a connector. Insertion monitor 30 is configured and arranged to close an electrical circuit when sensor 10, 10', 10" is properly inserted into the connector.

Insertion monitor 30 may have any suitable configuration, including but not limited to, a stripe extending across sensor strip 10, 10' from a side edge to a side edge, as illustrated in FIGS. 1, 2A, 2B, 3A, 3B and 5, a stripe extending across the sensor strip, although not the entire width, or an array of unconnected dots, strips, or other areas. The insertion monitor could have a long, tortuous path, which extends longitudinally toward an end of the sensor, rather than extending merely side-to-side. Additional information regarding insertion monitors can be found, for example, in U.S. Pat. No. 6,616,819.

In some embodiments, insertion monitor 30 is used to encode information regarding sensor strip 10, 10', 10".

Sensor Connection to Electrical Device

Figure 6:
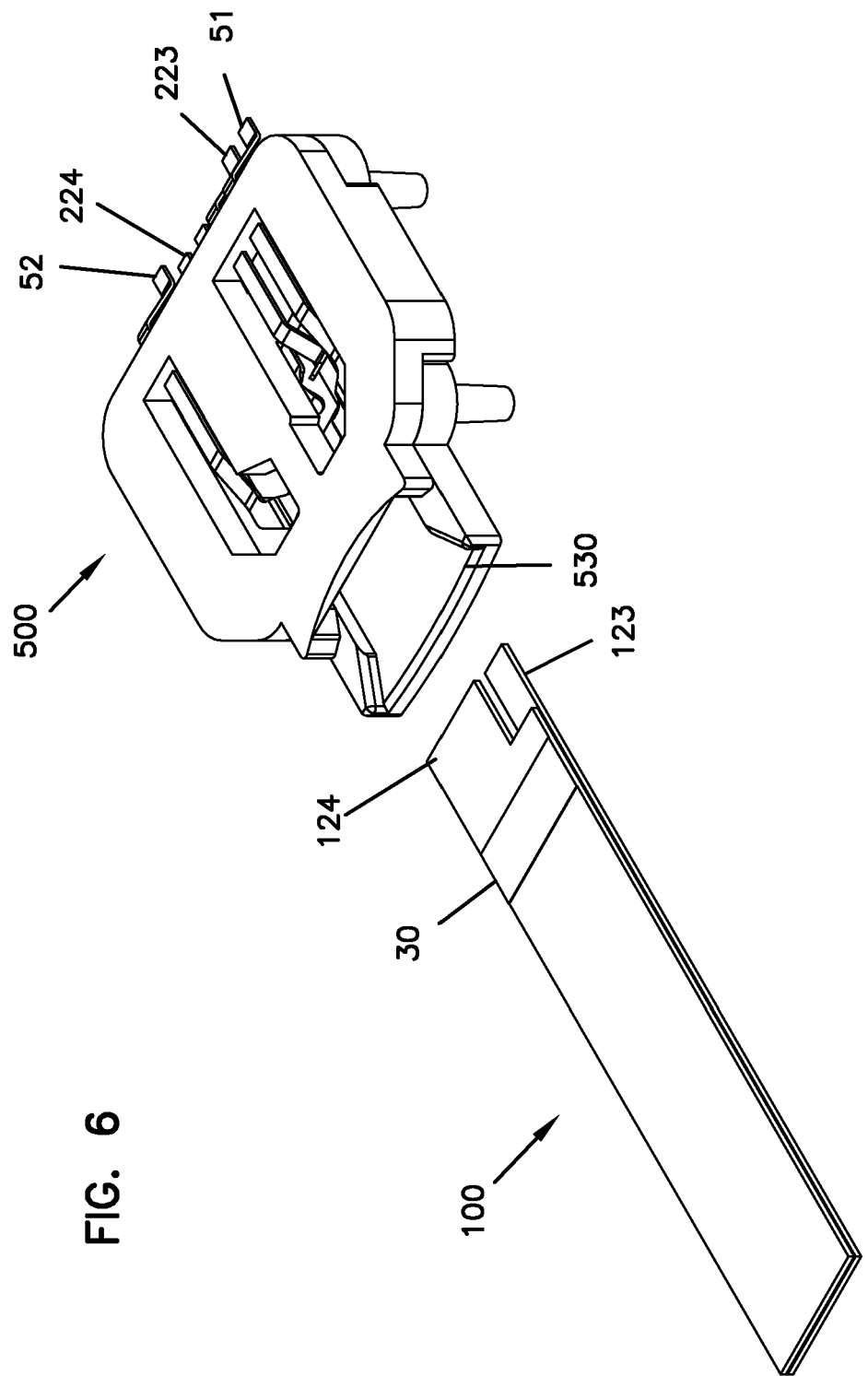
FIG. 6 is a top perspective view of a sensor strip positioned for insertion within an electrical connector device in accordance with the present disclosure.
Figure 10:
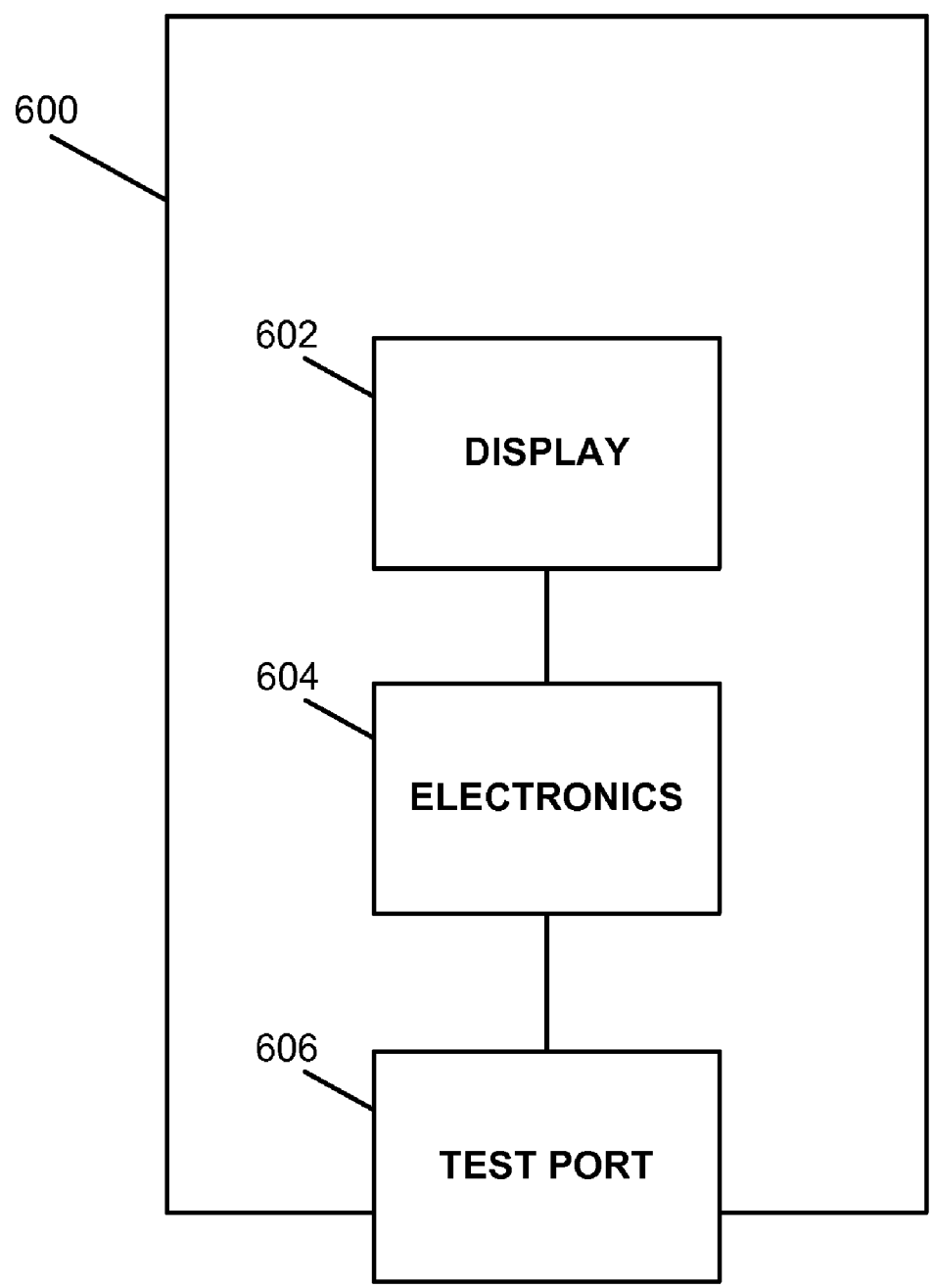
FIG. 10 is a schematic block diagram of a meter according to the present disclosure.

Referring to FIG. 6, a sensor strip 100 is illustrated readied for insertion into a connector 500. In some embodiments, connector 500 is a part of a meter. Specifically, connector 500 is a test port arranged and configured to receive a sensor strip 100. Sensor strip 100 is similar to sensor strips 10, 10', 10". Sensor strip 100 includes insertion monitor 30 on an outer surface of one of the substrates forming strip 100. Sensor strip 100 includes, although not illustrated, one working electrode and at least one counter electrode. The working electrode includes a contact pad positioned on tab 123 and the at least one counter electrode includes a contact pad positioned on tab 124. An example of a meter 600 is shown in FIG. 10, which includes a display 602, electronics 604, and a test port 606. Connector 500 (shown in FIG. 6) is an example of test port 606.

Sensor strip 100 is configured to couple to a meter (e.g., meter 600, shown in FIG. 10) or other electrical device by electrical connector 500 which is configured to couple with and contact the end of sensor 100 at the contact pads on tabs 123, 124. The sensor meter typically includes a potentiostat or other component to provide a potential and/or current for the electrodes of the sensor. The sensor reader also typically includes a processor (e.g., 604, shown in FIG. 10) such as a commercially available microprocessor or other electronic or hardware devices for determining analyte concentration from the sensor signals. The sensor meter also includes a display (e.g., 602, shown in FIG. 10) or a port for coupling a display (602) to the sensor. An example of a display is a liquid crystal display. The display displays the sensor signals and/or results determined from the sensor signals including, for example, analyte concentration, rate of change of analyte concentration, and/or the exceeding of a threshold analyte concentration (indicating, for example, hypo- or hyperglycemia).

Connector 500 includes leads or contact structures 51, 52 for connection to insertion monitor 30. Insertion monitor 30 is configured and arranged to close an electrical circuit between contact structures 51 and 52 when the sensor is properly inserted into the connector via receiver area 530. Proper insertion into connector 500 means that the sensor strip 100 is inserted right side up, that the correct end of strip 100 is inserted into connector 500, and that sensor strip 100 is inserted far enough into connector 500 that reliable electrical connections are made between the electrode contact pads on tabs 123, 124, and the corresponding contacts leads 223, 224. Preferably, no closed circuit is made unless all electrode pads have properly contacted the contact structures of connector 500. The insertion monitor may have shapes other than a stripe across the width of the sensor; for example, other designs include an individual dot, a grid pattern, or may include stylistic features, such as words or letters.

In an optional embodiment to ensure proper insertion of a sensor into a meter, the meter may include a raised area or bump that prevents or hinders the insertion of the sensor in an improper direction. Objects other than a raised area can also be used to guide the user in correct introduction of the sensor into the meter.

Additional information regarding connector devices can be found, for example, in U.S. Pat. No. 6,616,819.

In some possible embodiments, connector 500 is sized and/or shaped to accept only sensor strips 100 having a particular configuration. For example, receiver area 530 is sized to permit only sensor strips 100 having a corresponding size to enter receiver area 530. In another embodiment, receiver area 530 has a keyed configuration, such as including ridges, recesses, slots, and the like. In this embodiment, test strip 100 has corresponding ridges, recesses, slots, and the like that permit test strip 100 to be inserted into the keyed receiver area 530. The foregoing are some examples of a sensor recognition means, that permits the meter to recognize the sensor as a sensor that is compatible with the meter. Other examples of sensor recognition means include leads or contact structures (such as discussed above) that are capable of detecting one or more corresponding features of a sensor, such as a turn on bar, insertion monitor, contact pad, divot, protrusion, recess, unique shape, or other distinguishing characteristic of a sensor.

General Method for Manufacturing Sensors

Various methods for physically making sensor strips 10, 10', 10", 100 are known, and will not be discussed in detail herein. Generally, however, to make any of sensor strips 10, 10', 10", 100, two substrates 12, 14 are brought together, with spacer layer 15 therebetween; in most embodiments, sample chamber 20, 20' will be formed by an area void of spacer layer 15. Electrodes 22, 24 and any other electrical traces (e.g., fill indicator electrodes) are formed on one or both of substrates 12, 14 prior to combination. See for example, U.S. Pat. Nos. 6,618,934 and 6,616,819, for various methods to form sensor strips.

In accordance with some embodiments of the present disclosure, however, the sensors are made so that the user, or other external interaction, need not enter a calibration code into the meter in other equipment prior to using the sensor. Rather, the sensors have a slope and y-intercept (which relate to the calibration code) that is close to a slope and y-intercept that is predetermined and present in a meter. Thus, sensors designated as having a slope and y-intercept (having been predetermined at the manufacturing step) can be used with a meter that is configured with the same or similar slope and y-intercept.

Calibration of sensors, using slope and y-intercept, is well known. The calibration information or code of a sensor may relate to, e.g., the sensitivity of the sensor or to the y-intercept and/or slope of its calibration curve. The calibration code is used by the meter or other equipment to which the sensor, such as sensor strip 10, 10', 10", is connected to provide an accurate analyte reading. For example, based on the calibration code, the meter uses one of several programs stored within the meter.

It has been previously known to have each of the sensors from a batch of sensors have the same calibration code, so that the code is only entered or read once by the meter or other equipment. However, generally the calibration parameters vary from batch to batch due to variations in the composition of the active chemistry such as electron transfer agent and/or redox mediator, and/or variations in the inactive components such as buffers, salts, substrates, surfactants, electrode surface etc.

In accordance with this disclosure, batches of sensors that have calibration codes that fall within predetermined parameters (e.g., the No Cal Grid—a matrix of allowed range of slope and intercept values with respect to a fixed slope and intercept—described below) are suitable for use with meters or other equipment that are programmed for those calibration codes, and thus do not require coding by the user.

In one particular embodiment, for glucose sensor strips, if the calibration code falls within the parameters below, the sensor batch is acceptable for use with a predetermined meter, without having to input the calibration code into the meter. Rather, the meter already is configured to accept and accurately use a sensor that has the calibration code. In one embodiment, to meet the desired performance, at glucose levels >75 mg/dl, at least 90% of the sensors tested from the batch are within ±20% of reference, and at glucose ≦75 mg/dl, at least 90% of the sensors tested from the batch are within ±15 mg/dl of reference. In this way the sensors have at least a 90% probability of being within the desired range. In some embodiments, to meet the desired performance, at glucose levels >75 mg/dl, at least 95% of the sensors tested from the batch are within ±20% of reference, and at glucose ≦75 mg/dl, at least 95% of the sensors tested from the batch are within ±15 mg/dl of reference. In this way the sensors have at least a 95% probability of being within the desired range. In other embodiments, to meet the desired performance, at glucose levels >75 mg/dl, at least 97% or even 98% of the sensors tested from the batch are within ±20% of reference, and at glucose ≦75 mg/dl, at least at least 97% or even 98% of the sensors tested from the batch are within ±15 mg/dl of reference. In this way the sensors have at least a 97% or even a 98% probability of being within the desired range.

In other embodiments, at glucose levels >75 mg/dl, at least 90% of the sensors tested from the batch are within ±15% or 10% of reference, and at glucose ≦75 mg/dl, at least 90% of the sensors tested from the batch are within ±10 mg/dl of reference. In some embodiments, to meet the desired performance, at glucose levels >75 mg/dl, at least 95% of the sensors tested from the batch are within ±15% or 10% of reference, and at glucose ≦75 mg/dl, at least 95% of the sensors tested from the batch are within ±10 mg/dl of reference. In other embodiments, to meet the desired performance, at glucose levels >75 mg/dl, at least 97% or even 98% of the sensors tested from the batch are within ±15% or 10% of reference, and at glucose ≦75 mg/dl, at least at least 97% or even 98% of the sensors tested from the batch are within ±10 mg/dl of reference.

The measurement offset is contributed by a combination of sensor calibration offset and clinical variations of the measurement. The clinical variations consist of sensor variations (e.g., sensor strip variations), testing technique variations and sample (blood-to-blood) variations. All these variations can be characterized as random variations with a normal distribution.

Figure 7:
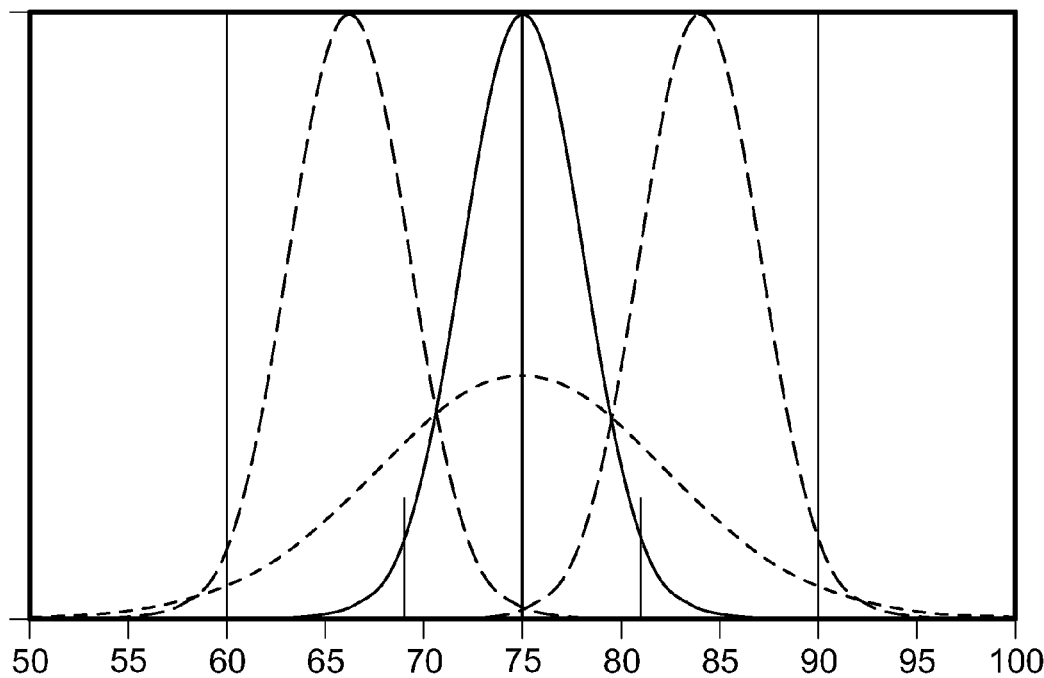
FIG. 7 is a graphical distribution of results around the calibration position based on standard deviation.

With a known measurement variation and the allowable calibration range (e.g., at least 90% within ±20% of reference), the center of the normal distribution can be determined. The normal distribution will have, for example, 90% or 95% data within +/−2 SD (standard deviation) from the center. FIG. 7 is an illustration of the effect of standard deviation on an allowed calibration position. For example, using the desired parameters from above, at 75 mg/dl glucose, a SD of 7.5 mg/dl measurement variation will require the calibration to be right on the center, at 75 mg/dl, to meet the +/−15 mg/dl requirement. On the other hand, a SD of 3.0 mg/dl measurement variation will allow the calibration to vary from 66 mg/dl to 84 mg/dl and still meet the +/−15 mg/dl requirement.

Figure 8:
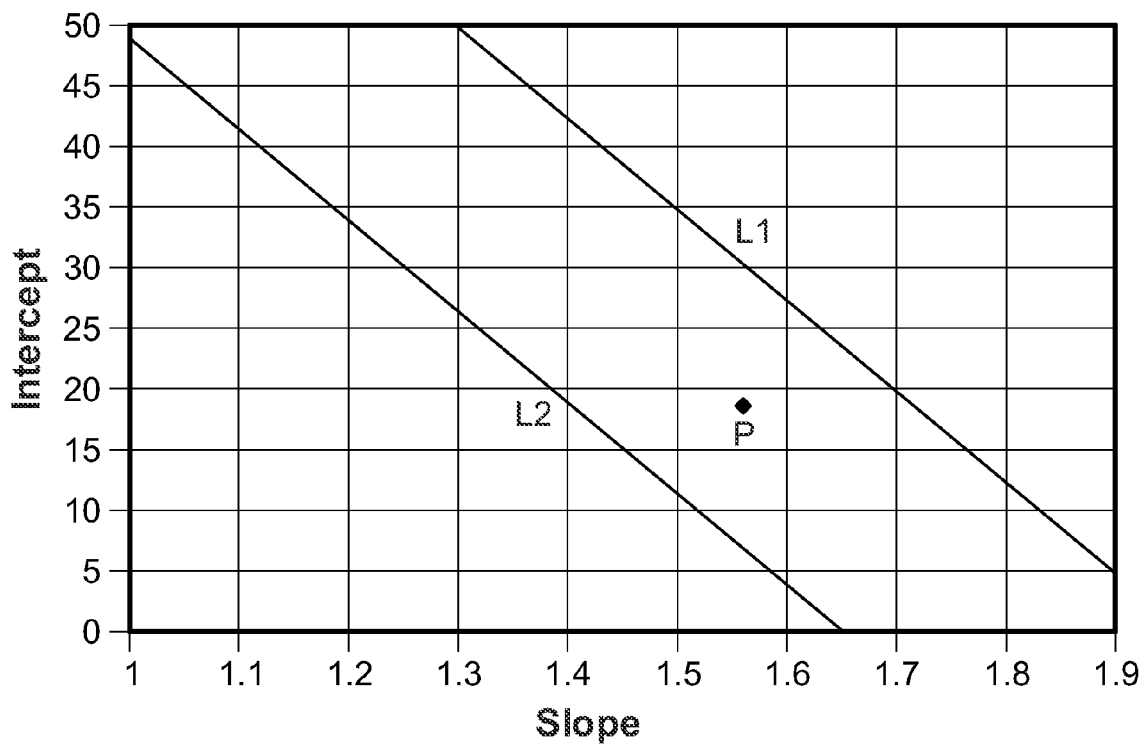
FIG. 8 is a graphical range of slope and intercept with respect to a fixed point that would meet the ISO requirements at a given glucose level.

In a slope-intercept space, this range can be defined with a pair of parallel lines, L1 and L2, as shown in FIG. 8. A sensor lot with calibration slope-intercept between the lines L1, L2 will meet the requirement at this analyte (e.g., glucose) level with a meter calibrated at slope-intercept P.

To determine L1 and L2 of FIG. 8, it is assumed that:
Ps—meter slope
Pi—meter intercept
Ss—sensor slope
Si—sensor intercept
G—sample glucose in mg/dl
Gm—meter calculated glucose value in mg/dl
SD—measurement variation in standard deviation form (mg/dl)
CV—measurement variation in % CV form (%)
Thus, L1 and L2 can be derived from following:

$$G \cdot Ss + Si = Gm \cdot Ps + Pi, \text{ (both sides are measured charge)}$$

$$Si = (Gm \cdot Ps + Pi) - G \cdot Ss$$

For L1:

$$Gm = G + (15 - 2 \cdot SD) \text{ when } G < 75 \text{mg/dl}$$

$$Gm = G \cdot (1 + (20\% - 2 \cdot CV)) \text{ when } G > 75 \text{mg/dl}$$

For L2:

$$Gm = G - (15 - 2 \cdot SD) \text{ when } G < 75 \text{mg/dl}$$

$$Gm = G \cdot (1 - (20\% - 2 \cdot CV)) \text{ when } G > 75 \text{mg/dl}$$

At any given analyte (e.g., glucose) level, a pair of parallel lines can be described using the above formula, which define the sensor's slope-intercept range that meets the glucose measurement requirement at the given glucose level.

Figure 9:
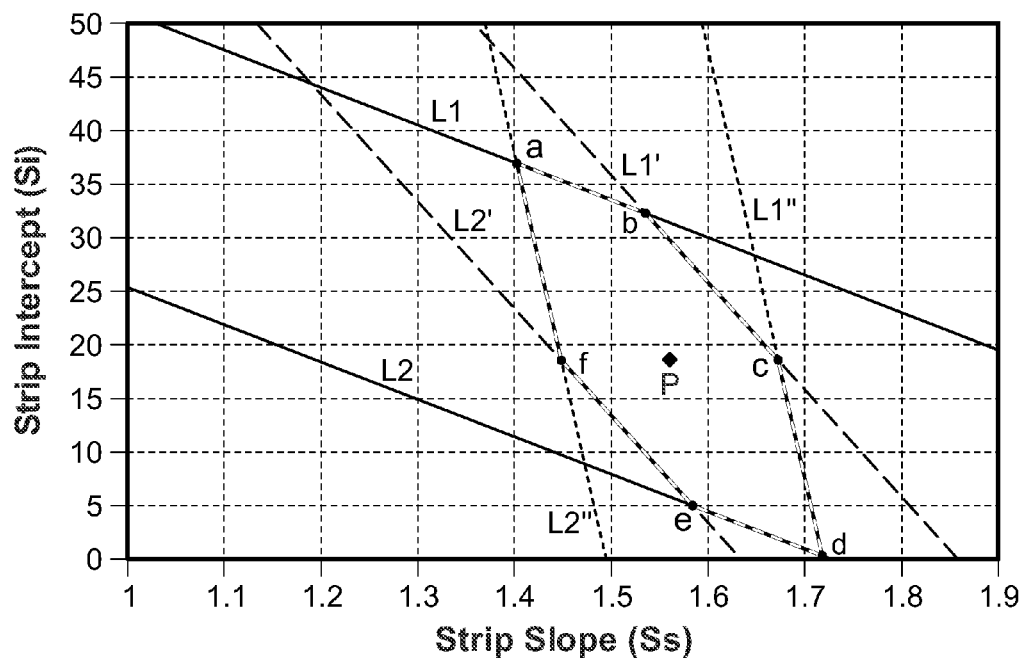
FIG. 9 is a graphical range of slope and intercept with respect to a fixed point that would meet the ISO requirements at multiple glucose levels.

If, for example, three glucose levels are selected (for example, at 35, 100 and 400 mg/dl), corresponding three pairs of lines will cross each other and form a closed area defined by points a, b, c, d, e and f (see FIG. 9). This closed area is the area in which calibration codes fall within predetermined parameters, also referred to as "No Cal Grid" herein. The meter calibration slope-intercept P (also illustrated in FIG. 8) is present at the center of this area. Any sensor lot whose calibration slope-intercept falls within the area or grid will meet the measurement requirement at all these glucose levels. Properly spaced, three glucose levels can reasonably cover the whole glucose range.

For example:

if $SD=3.4$ mg/dl, and $CV=6.4\%$ $Ps=1.56$ and $Pi=18.6$

At 35 mg/dl:

$L1: Si=(43.2\times 1.56+18.6)-35\cdot Ss=85.99-35\cdot Ss$ $L2: Si=(26.8\times 1.56+18.6)-35\cdot Ss=60.41-35\cdot Ss$ At 100 mg/dl:

$L1': Si=(107.2\times 1.56+18.6)-100\cdot Ss=185.83-100\cdot Ss$ $L2': Si=(92.8\times 1.56+18.6)-100\cdot Ss=163.37-100\cdot Ss$ At 400 mg/dl:

$L1'': Si=(428.8\times 1.56+18.6)-400\cdot Ss=687.55-400\cdot Ss$ $L2'': Si=(371.2\times 1.56+18.6)-400\cdot Ss=579.70-400\cdot Ss$ The six cross points (a, b, c, d, e and f in FIG. 9) can be easily resolved using the above six equations.

Any sensor lot that has a slope and intercept that falls within the six corners of the grid area will give clinically accurate result when tested using the meter that has the fixed slope and intercept. Not all sensors in a lot or batch need be tested to determine whether the slope and intercept fall within the grid area. Typically, at least one sensor from a lot or batch is tested, often 10 sensors, to determine whether or not the slope and intercept fall within the grid area. In some embodiments, 1% of the sensors in the lot are tested. As described above, the slope and intercept within a sensor batch does not appreciably vary.

Using the theory above, batches of sensors can be manufactured and sold, for use with predetermined meters, that do not require any active input of the calibration code into the meter. Rather, the sensor has a calibration code that is acceptably close to that of the meter.

In order to perform a test, the user would merely have to connect the sensor with the meter, and test a fluid sample. The user would not have to actively input any information, such as adjust the calibration code on the meter to match that of the sensor, use a chip to calibrate the meter to the specific sensor lot, or use a calibrator to calibrate the meter to the specific sensor lot. Additionally, the sensor packaging would not need the calibration information present thereon. Further, the meter would not need to read the calibration information from either the user, or from the sensor itself or its packaging.

Application of the Sensor

A common use for the analyte sensor according embodiments of the present disclosure, such as sensor strip 10, 10', 10", 100 is for the determination of analyte concentration in a biological fluid, such as glucose concentration in blood, interstitial fluid, and the like, in a patient or other user. Sensor strips 10, 10', 10", 100 may be available at pharmacies, hospitals, clinics, from doctors, and other sources of medical devices. Multiple sensor strips 10, 10', 10", 100 may be packaged together and sold as a single unit; e.g., a package of 25, 50, or 100 strips.

Sensor strips 10, 10', 10", 100 can be used for an electrochemical assay, or, for a photometric test. Sensor strips 10, 10', 10", 100 are generally configured for use with an electrical meter, which may be connectable to various electronics. A meter may be available at generally the same locations as sensor strips 10, 10', 10", 100 and sometimes may be packaged together with sensor strips 10, 10', 10", 100, e.g., as a kit.

In some embodiments, the meter includes meter electronics such as a signal generator, a detector, and a signal processor. A signal generator applies a first signal to the sensor. The sensor, having a sample containing an analyte of interest, allows the first signal to interact with the sample. A detector then detects a second signal after it has interacted with the sample. The second signal is then analyzed by the signal processor. The signal processor determines the concentration of the analyte based at least in part on the second signal, as well as a single fixed slope value and a single fixed intercept value. The single fixed slope value and the single fixed intercept value are used for determining the concentration of an analyte independent of the particular sensor being used. In some embodiments, the single fixed slope value and the single fixed intercept value do not change after manufacturing of the meter has been completed.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device does have a display, such as a liquid crystal display (LCD), as well as an input device, such as buttons, a keyboard, mouse or touch-screen. With such an arrangement, the user can control the meter indirectly by interacting with the user interface(s) of the server device, which in turn interacts with the meter across a wireless link.

The server device can also communicate with another device, such as for sending glucose data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as sensor strips 10 and the meter, and sometimes may be packaged together with sensor strips 10 and/or meter, e.g., as a kit.

Integrated Sample Acquisition and Analyte Measurement Device

An analyte measurement device constructed according to the principles of the present disclosure typically includes a sensor strip 10, 10', 10", 100, as described hereinabove, combined with a sample acquisition apparatus to provide an integrated sampling and measurement device. The sample acquisition apparatus typically includes, for example, a skin piercing member, such as a lancet, that can be injected into a patient's skin to cause blood flow. The integrated sample acquisition and analyte measurement device can comprise a lancing instrument that holds a lancet and sensor strip 10, 10', 10", 100. The lancing instrument might require active cocking. By requiring the user to cock the device prior to use, the risk of inadvertently triggering the lancet is minimized. The lancing instrument could also permit the user to adjust the depth of penetration of the lancet into the skin. Such devices are commercially available from companies such as Boehringer Mannheim and Palco. This feature allows users to adjust the lancing device for differences in skin thickness, skin durability, and pain sensitivity across different sites on the body and across different users.

In one embodiment, the lancing instrument and the meter are integrated into a single device. To operate the device the user need only insert a disposable cartridge containing a sensor strip and lancing device into the integrated device, cock the lancing instrument, press it against the skin to activate it, and read the result of the measurement. Such an integrated lancing instrument and test reader simplifies the testing procedure for the user and minimizes the handling of body fluids.

In some embodiments, sensor strips 10, 10', 10" may be integrated with both a meter and a lancing device. Having multiple elements together in one device reduces the number of devices needed to obtain an analyte level and facilitates the sampling process.

For example, embodiments may include a housing that includes one or more of the subject strips, a skin piercing element and a processor for determining the concentration of an analyte in a sample applied to the strip. A plurality of strips 10, 10', 10", 100 may be retained in a cassette in the housing interior and, upon actuation by a user, a single strip 10, 10', 10" may be dispensed from the cassette so that at least a portion extends out of the housing for use.

Operation of the Sensor

In use, a sample of biological fluid is provided into the sample chamber of the sensor, where the level of analyte is determined. The analysis may be based on providing an electrochemical assay or a photometric assay. In many embodiments, it is the level of glucose in blood that is determined. Also in many embodiments, the source of the biological fluid is a drop of blood drawn from a patient, e.g., after piercing the patient's skin with a lancing device, which could be present in an integrated device, together with the sensor strip.

The analyte in the sample is, e.g., electrooxidized or electroreduced, at working electrode 22, and the level of current obtained at counter electrode 24 is correlated as analyte concentration.

Sensor strip 10, 10', 10", 100 may be operated with or without applying a potential to electrodes 22, 24. In one embodiment, the electrochemical reaction occurs spontaneously and a potential need not be applied between working electrode 22 and counter electrode 24. In another embodiment, a potential is applied between working electrode 22 and counter electrode 24.

All patents and other references in this specification are indicative of the level of ordinary skill in the art to which this disclosure pertains. All patents and other references are herein incorporated by reference to the same extent as if each individual patent or reference was specifically and individually incorporated by reference.

What is claimed:

1. A method of determining an analyte concentration in a sample, comprising:
   providing a meter having a single defined slope value and single defined intercept value;
   selecting a sensor from a plurality of sensor lots, said sensor having a slope value and an intercept value, wherein the slope value and the intercept value are equal to or substantially similar to the single defined slope and the single defined intercept; inserting the sensor into the meter; providing the sample to the sensor; and determining the analyte concentration in the sample without communicating a calibration code to the meter.

2. The method of claim 1 wherein determining the analyte concentration in the sample without communicating the calibration code to the meter comprises determining the analyte concentration in the sample without the meter actively reading the calibration code.

3. The method of claim 1, wherein determining the analyte concentration in the sample without the meter actively reading the calibration code includes determining the analyte concentration in the sample without the meter actively reading the calibration code from the sensor or sensor package.

4. The method of claim 1, wherein selecting a sensor comprises selecting a sensor having a volume of no more than about 1 μL.

5. The method of claim 1, wherein selecting a sensor comprises selecting a sensor having a volume of no more than about 0.5 μL.

6. The method of claim 1, wherein selecting a sensor comprises selecting a sensor having a volume of no more than about 0.3 μL.

7. The method of claim 1, wherein selecting a sensor comprises selecting a sensor having a volume of no more than about 0.1 μL.

8. The method of claim 1, wherein selecting a sensor comprises selecting a tip-fill sensor.

9. The method of claim 1, wherein selecting a sensor comprises selecting a side-fill sensor.

10. The method of claim 1, wherein selecting a sensor comprises selecting a top-fill sensor.

11. The method of claim 1, wherein determining the analyte concentration in the sample comprises determining the concentration of analyte in the sample by coulometry.

12. The method of claim 1, wherein determining the analyte concentration in the sample comprises determining the concentration of analyte in the sample by amperometry.

13. The method of claim 1, wherein determining the analyte concentration in the sample comprises determining the concentration of analyte in the sample by potentiometry.

14. The method of claim 1, wherein determining the analyte concentration in the sample comprises determining a concentration of glucose in a sample of blood.

* * * * *